(12) United States Patent
Platzek et al.

(10) Patent No.: US 7,199,268 B2
(45) Date of Patent: Apr. 3, 2007

(54) PROCESS FOR THE PRODUCTION OF DENDRITIC TRIMESIC ACID TRIAMIDES

(75) Inventors: Johannes Platzek, Berlin (DE); Klaus-Dieter Graske, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 89 days.

(21) Appl. No.: 11/012,737

(22) Filed: Dec. 16, 2004

(65) Prior Publication Data

US 2005/0238615 A1  Oct. 27, 2005

Related U.S. Application Data

(60) Provisional application No. 60/536,503, filed on Jan. 15, 2004.

(30) Foreign Application Priority Data

Dec. 16, 2003  (DE) ................ 103 61 140

(51) Int. Cl.
*C07C 233/05* (2006.01)
*C07C 231/02* (2006.01)

(52) U.S. Cl. .............. 564/153; 564/133; 424/78.08

(58) Field of Classification Search ............ 564/153, 564/133; 424/78.08
See application file for complete search history.

(56) References Cited

U.S. PATENT DOCUMENTS 5,364,614 A    11/1994  Platzek et al.
5,527,524 A    6/1996   Tomalia et al.
6,063,361 A    5/2000   Schmitt-Willich et al.
6,248,306 B1   6/2001   Schmitt-Willich et al.
6,818,203 B2 * 11/2004  Platzek et al. .......... 424/9.363

FOREIGN PATENT DOCUMENTS

| DE | 4344460 | 6/1995 |
|----|---------|--------|
| DE | 4425857 | 1/1996 |
| EP | 0430863 A | 6/1991 |
| WO | WO 9524225 | 9/1995 |
| WO | WO 9528966 | 11/1995 |
| WO | WO 97/02051 | 1/1997 |

OTHER PUBLICATIONS

B. Raduechl et al., "Synthesis and characterization of novel dendrimer-based gadolinium complexes as MRI contrast agents for the vascular system," Polymeric Materials Science and Engineering, 1998, pp. 516-517, vol. 79, XP002323487.

Wiener E C et al., "Dendrimer-based metal chelates: a new class of magnetic resonance imaging contrast agents," Magnetic Resonance in Medicine, Jan. 1, 1994, pp. 1-8, vol. 31, No. 1, XP000423671.

* cited by examiner

*Primary Examiner*—Shailendra Kumar

(57) ABSTRACT

A new process for the production of dendritic trimesic acid triamides is described.

20 Claims, No Drawings

PROCESS FOR THE PRODUCTION OF DENDRITIC TRIMESIC ACID TRIAMIDES

This application claims the benefit of the filing date of U.S. Provisional Application Ser. No. 60/536,503 filed Jan. 15, 2004 which is incorporated by reference herein.

The invention relates to the subject that is characterized in the claims, i.e., primarily a new process for the production of dendritic trimesic acid triamides.

The use of cascade polymers (dendritic metal complexes) for the visualization of the intravascular space (blood pool imaging) is one of the important applications in MRI angiography. The synthesis of such dendritic metal complexes is described in, e.g., EP 0430863 and WO 97/02051. Of the many examples mentioned there, Example 1 (from WO 97/02051) has become particularly important. This molecule, which had become known among experts as Gadomer (or else Gadomer 17), is found in phase II of the clinical examination for cardiac imaging indication. The visualization of coronaries in the heart is a very important method in early diagnosis. Unfortunately, to date highly invasive x-ray technology (with catheter insertion/x-ray exposure) must be used to perform such studies. In this indication there is, however, a great "medical need" for compounds that can be used in MR tomography, whereby the contrast medium must be injected only i.v. The use of Gadomer as a contrast medium for MRI had been described in many publications and papers. For example, there can be mentioned:

1. Clarke, S. E.; Weinmann, H. J.; Dai, E.; Lucas, A. R.; Rutt, B. K. Comparison of Two Blood Pool Contrast Agents for 0.5-T MR Angiography: Experimental Study in Rabbits. Radiology 214: 787–794 (2000).

2. Dong, Q.; Hurst, D. R.; Weinmann, H.-J.; Chevenet, T. L.; Lonny, F. J.; Prince, M. R. Magnetic Resonance Angiography With Gadomer-17. An Animal Study Original Investigation. Investigative Radiology, Vol. 33, No. 9, pp. 699–108 (1998).

3. Abolmaali, N. D.; Hietschold, V.; Appold, S.; Ebert, W.; Vogl, T. J. Gadomer-17-Enhanced 3D Navigator-Echo MR Angiography of the Pulmonary Arteries in Pigs. Eur Radiol 12: 692–697 (2002).

4. Fink, C.; Kiessling, F.; Bock, M.; Lichy, M. P.; Misselwitz, B.; Peschke, P.; Fusenig, N. E.; Grobholz, R.; Delorme, S. High-Resolution Three-Dimensional MR Angiography of Rodent Tumors: Morphologic Characterization of Intratumoral Vasculature. J Magn Reson Imaging 18: 59–65 (2003).

5. Weinmann, H.-J.; Ebert, W.; Wagner, S.; Taupitz, M.; Misselwitz, B., Schmitt-Willich, H. MR Angio with Special Focus on Blood Pool Agents. Proceedings of the 9th Annual International Workshop on Magnetic Resonance Angiography; Oct. 7–11, 1997, Valencia, Spain.

6. Woodard, P. K.; Li, D.; Zheng, J.; Abendschein, D.; Haacke, E. M.; Mintorovitch, J., Weinmann, H.-J.; Gropler, R. J. Stenosis Detection Using Gadomer-17-Enhanced Coronary MR Angiography. Proceedings of ISMRM, 7th Scientific Meeting and Exhibition; May 22–28, 1999, Philadelphia, USA.

7. Li, D.; Zheng, J.; Weinmann, H. J. Contrast-Enhanced MR Imaging of Coronary Arteries: Comparison of Intra- and Extravascular Contrast Agents in Swine. Radiology 218: 670–678 (2001).

8. Schnorr, J.; Wagner, S.; Ebert, W.; Heyer, C.; Laub, G.; Kivelitz, D.; Abramjuk, C.; Hamm, B.; Taupitz, M. MR Angiography of the Coronary Arteries: Comparison of the Blood Pool Contrast Medium Gadomer and Gd-DTPA in Pigs. Rofo Fortschr Geb Rontgenstr Neuen Bildgeb Verfahr 175: 822–829 (2003).

9. Jerosch-Herold, M.; Wilke, N.; Wang, Y.; Gong, G. R.; Mansoor, A. M.; Huang, H.; Gurchumelidze, S.; Stillman, A. E. Direct Comparison of an Intravascular and an Extracellular Contrast Agent for Quantification of Myocardial Perfusion. Cardiac MRI Group. Int J Card Imaging 1999; 15:453–464.

10. Roberts, H. C.; Saeed, M.; Roberts, T. P.; Muehler, A.; Brasch, R. C. MRI of Acute Myocardial Ischemia: Comparing a New Contrast Agent, Gd-DTPA-24-Cascade Polymer, with Gd-DTPA. J Magn Reson Imaging 9: 204–208 (1999).

11. Gerber, B. L.; Bluemke, D. A.; Chin, B. B.; Boston, R. C.; Heldman, A. W., Lima, J. A.; Kraitchman, D. L. Single-Vessel Coronary Artery Stenosis: Myocardial Perfusion Imaging with Gadomer-17 First-Pass MR Imaging in a Swine Model of Comparison with Gadopentetate Dimeglumine. Radiology 225: 104–112 (2002).

Within the context of the development of this compound, a need for increasingly larger amounts of substance developed. Since the substance is administered to humans, strict standards must be set on the purity of the end product as well as on the intermediate products. Because of the many uses that are to be expected, such a high-grade product should also be producible at a representative (in price) expense. There is therefore the desire to have available as economically advantageous a synthesis as possible.

A very important intermediate product of the synthesis of Gadomer is the so-called Z-24-amine (Example 1d from WO 97/02051), since it contains the complete skeleton of the dendrimer:

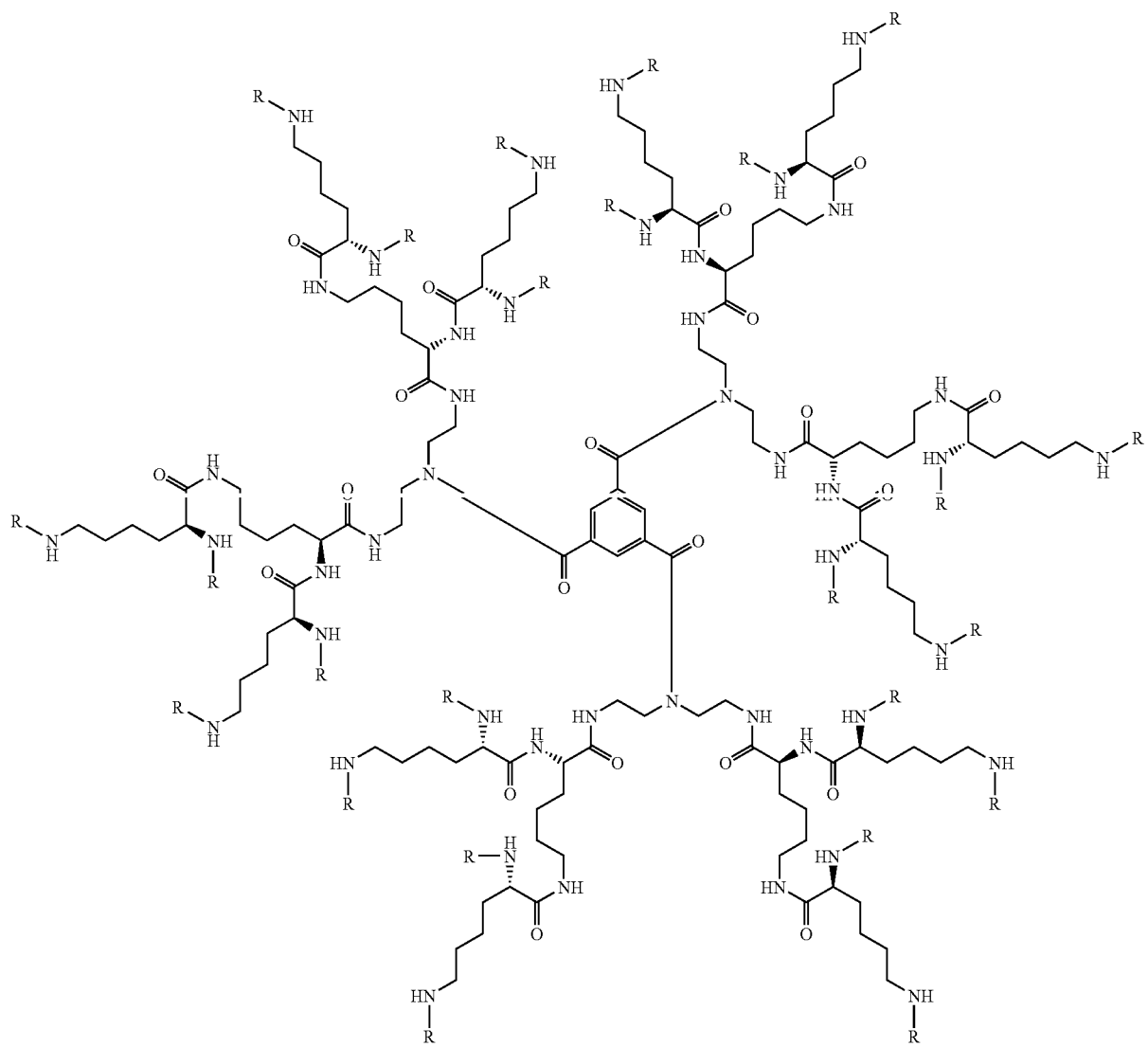
R = Z
After the Z-protective groups (—CO—OCH$_2$—C$_6$H$_5$) are cleaved, the amine is converted into the target compound Gadomer by reaction with active esters of complexing agents. The latter is described in WO 97/02051 and WO 98/24775.
The synthesis of this intermediate compound is described by way of example in Example 1 of WO 97/02051:
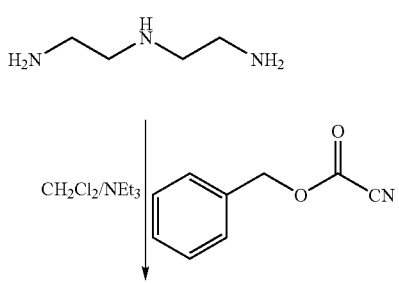

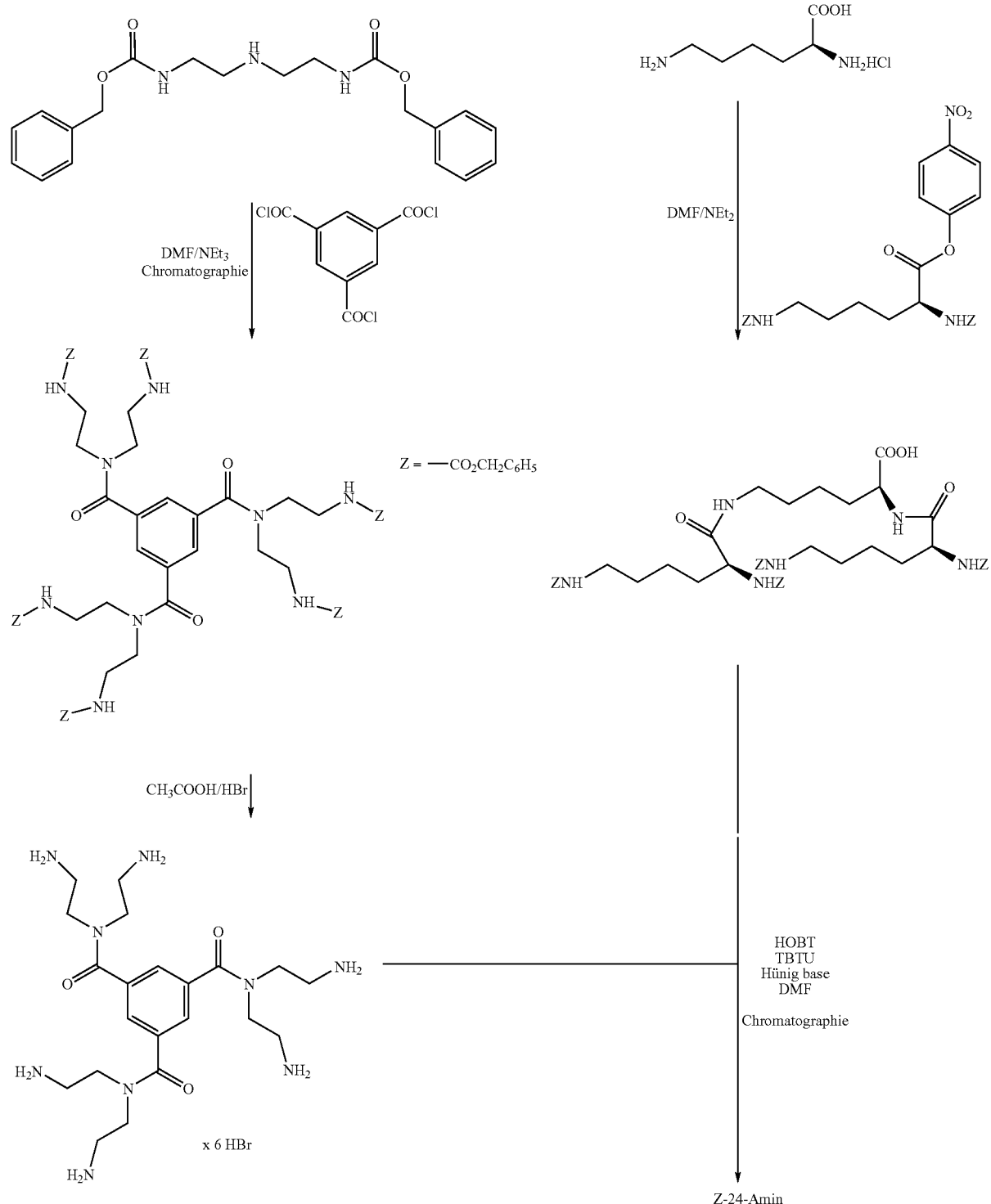

[Key:]
Chromatographie = Chromatography
Z-24-Amin = Z-24-Amine

A major drawback of this synthesis is the use of highly toxic and very expensive benzyloxycarbonylnitrile. In addition, during linkage of the trilysyl component (last stage), considerable racemization (~10–20%) on the alpha-C-atom of lysine is observed. This results in diastereomer mixtures that are difficult to separate, by which the total yield is drastically reduced. Such a synthesis method is therefore not acceptable for an upscaling in the multi-kg range both from the environmental standpoint and for economic reasons. The total yield over all stages (starting from diethylenetriamine) is only 14% in a purity of about 95% (to achieve a desired purity of 98%, additional very high losses can be expected during chromatography).

A slight improvement with respect to avoiding racemization in the case of the introduction of the outside lysine shell yielded the sequence below, which was presented at the American Chemical Society Convention, international meeting, New York 2003 (paper by J. Platzek):

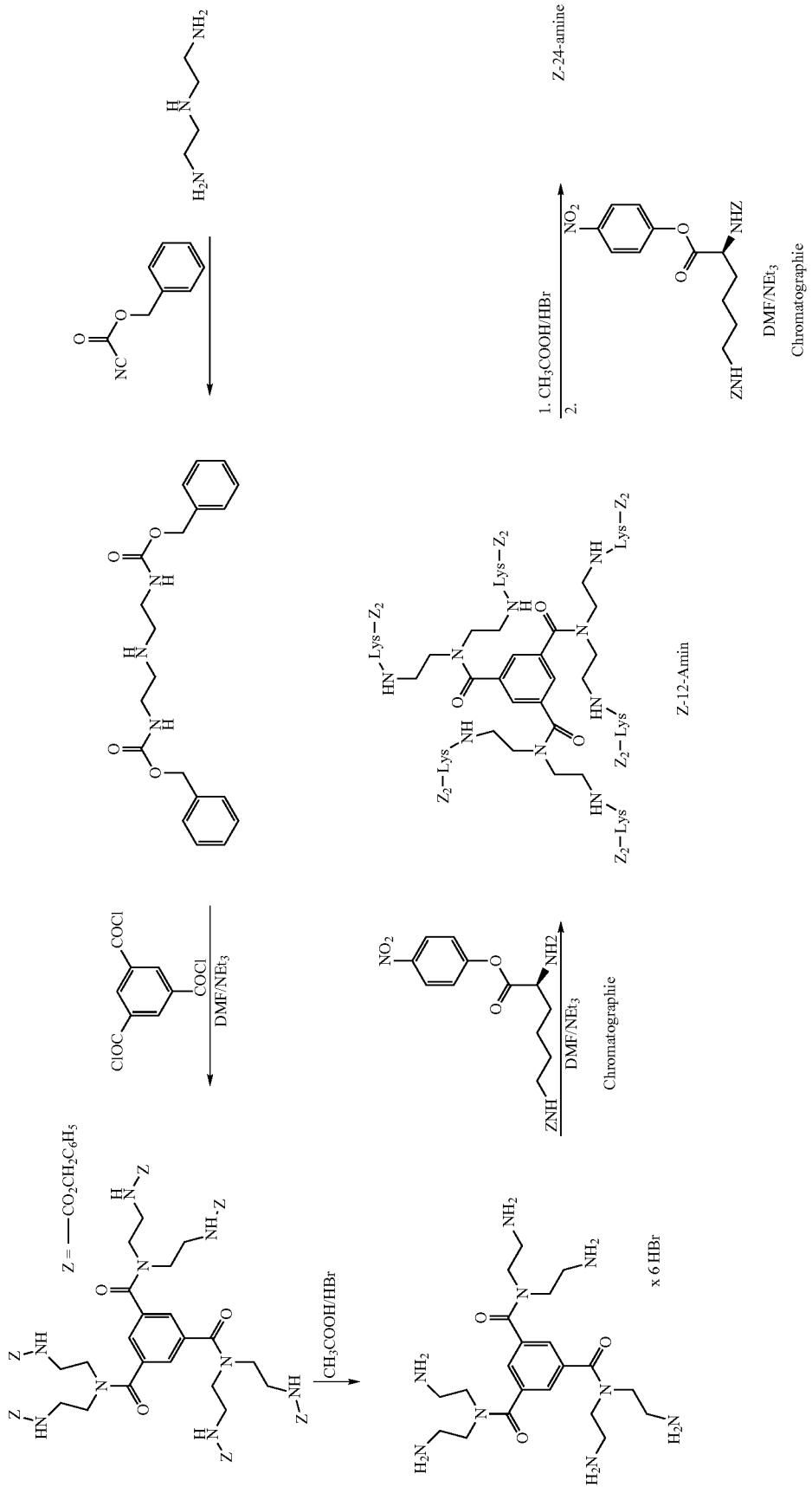

[Key:]
Chromatographie=Chromatography
Z-24-Amine=Z-24-Amines
Z-12-Amin=Z-12-Amine In addition, benzyloxycarbonylnitrile is used, but loss-prone chromatographies (because of numerous similar by-products) are necessary to obtain Z-24-amine material according to specifications (98% purification according to HPLC). The total yield, however, in addition is not satisfactory for an upscaling. It is 21% over all stages (starting from diethylenetriamine).

Another alternative was presented at the American Chemical Society, international meeting, New York 2003 (paper by J. Platzek):

This variant avoids the use of benzyloxycarbonynitrile, but in addition, two relatively expensive chromatographic purifications are necessary for separation from several structurally very similar by-products. These syntheses could be used successfully in the glass industry for the production of the first 1–2 kg of Gadomer. In further upscaling, however, it then very quickly turned out that even this method is uneconomical because of two expensive chromatography stages. The total yield over all stages (starting from diethylenetriamine) is only 31%.

To move ahead with the Gadomer project successfully (i.e., to make possible the production of more than 1000 kg of product/year after introduction on the market), a cost-effective synthesis for the Z-24-amine must be developed.

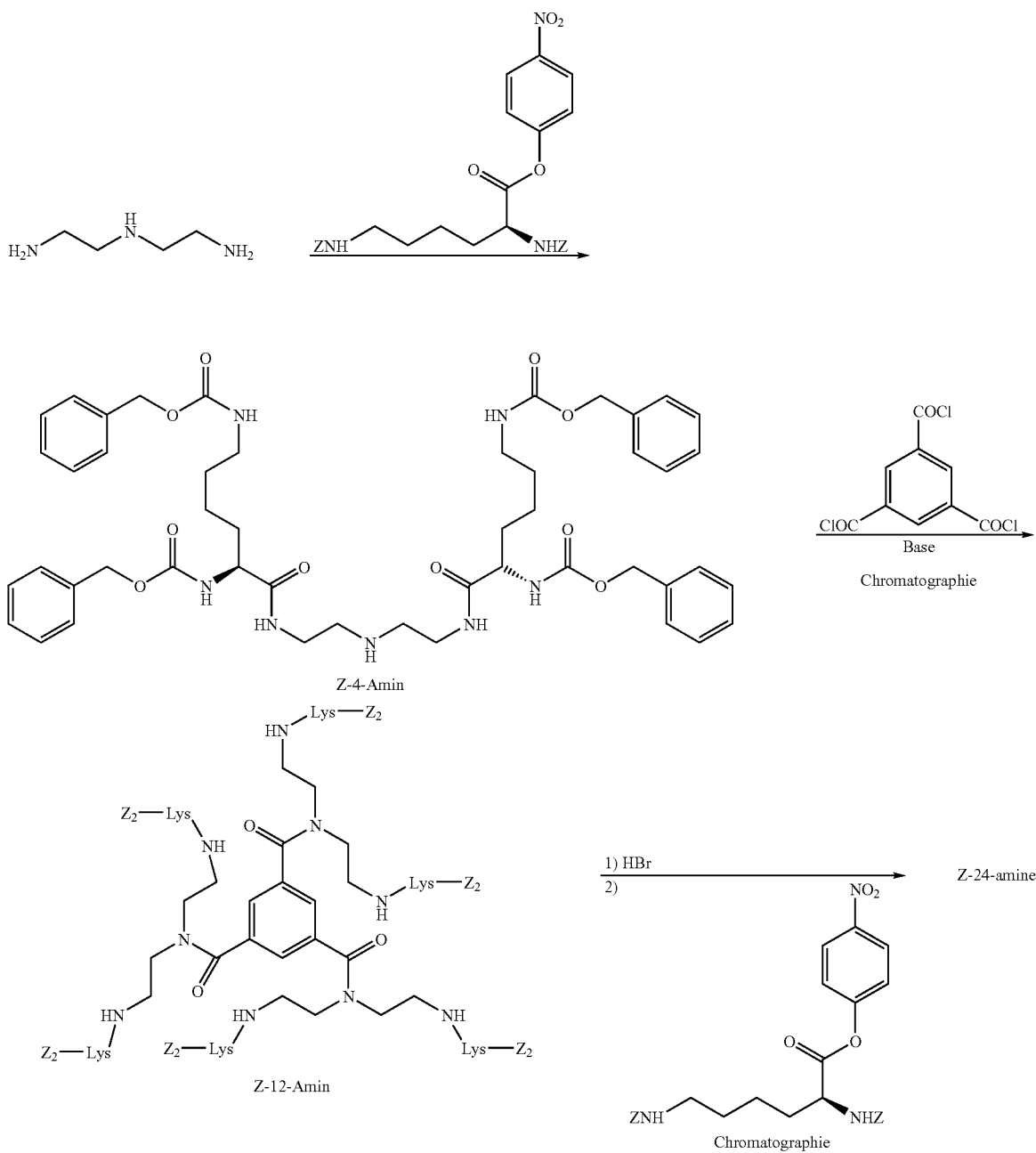

This process with use of the new intermediate product Z-8-amine (compound III) meets the set requirements to a large extent.

Compounds of general formula I

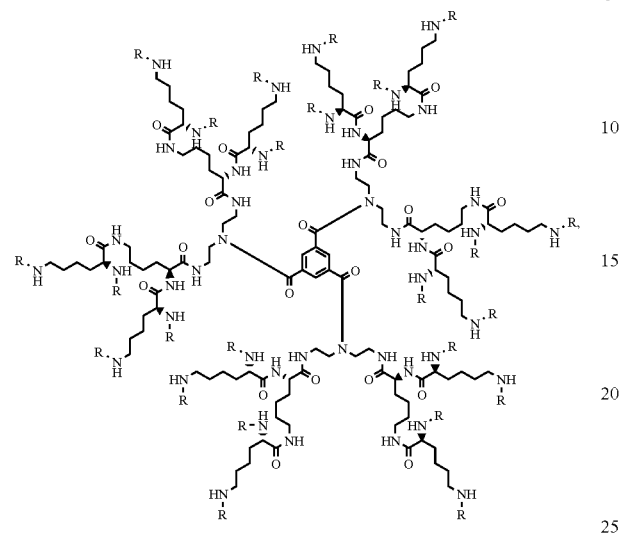

(I)

in which R stands for a Z or a Boc protective group, are obtained by compounds of general formula II

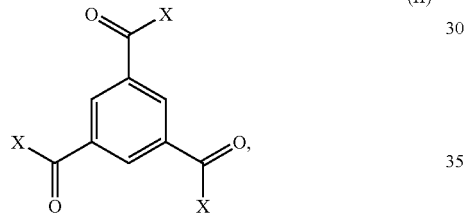

(II)

in which X stands for a Cl, Br, or F atom or a 4-nitrophenol, N-succinimide, imidazole, or pentafluorophenol group, but preferably for a chlorine atom, being reacted with compounds of general formula III

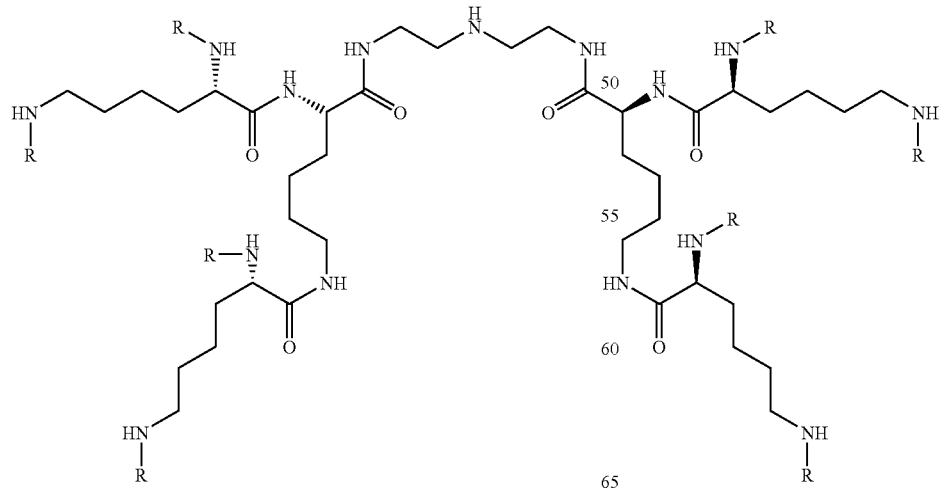

(III)

The reaction is carried out according to the processes, known to one skilled in the art, of reacting activated aromatic acids with secondary amines, see, e.g.: Guzei, Ilia A.; Li, Kelin; Bikzhanova, Galina A.; Darkwa, James; Mapolie, Selwyn F.; Dalton Trans.; 4; 2003; 715–722.;

Ried; Koenigstein; Chem. Ber.; 92; 1959; 2532, 2538.

Azumaya, Isao; Kagechika, Hiroyuki; Yamaguchi, Kentaro; Shudo, Koichi; Tetrahedron; 51; 18; 1995; 5277–5290.

Matsunaga, Yoshio; Miyajima, Nobuhiko; Nakayasu, Yuichi; Sakai, Satoshi; Yonenaga, Michihiro; Bull. Chem. Soc. Jpn.; 61; 1; 1988; 207–210.

Rehse, Klaus; Woyke, Christian; Rodloff, Arne; Hahn, Helmut; Arch. Pharm. (Weinheim Ger.); 329; 3; 1996; 155–160.

Rehse, Klaus; Luekens, Ute; Claus, Gudrun; Arch. Pharm. (Weinheim Ger.); 320; 12; 1987; 1233–1238.

Ebmeyer, Frank; Voegtle, Fritz; Chem. Ber.; 122; 1989; 1725–1728.

Used as solvents are non-protic solvents, such as, e.g., THF, 1-methyl-THF, tetrahydropyran, dichloromethane, 1,2-dimethoxyethane, dioxane, acetonitrile, propionitrile, and chloroform. THF is preferred.

Used as acid traps are either organic bases, such as triethylamine, Hünig base, tributylamine, pyridine, or lutidine, or inorganic bases, such as sodium carbonate, potassium carbonate, or lithium carbonate, which are added to the reaction solution in solid form. The reaction is carried out at temperatures of 0–100° C., but preferably at 50–80° C. The reaction time is 30 minutes to 5 hours; 30 minutes to 2.5 hours are preferred.

The purification of such crude products that are obtained is performed preferably by chromatography on normal or reversed-phase phases. Preferred is a reversed-phase chromatography with water-miscible mobile solvents, such as methanol, ethanol, acetonitrile, isopropanol, acetone and their mixtures with water. Preferred is a mixture that consists of water/methanol. The product can be isolated by spray-drying or else in solution (by redistillation on the subsequent solvent).

The new process allows the key compounds Z-24-amine and the analogous Boc-24-amine to be produced on an industrial scale. The total yields that are achieved are excellent and thus allow an economically and ecologically advantageous implementation. The use of the new protected 8-amines of general formula III as intermediate compounds allows the production of very pure crude products, whereby the chromatography of the final stage is very simplified. Purities of more than 98% in very high yields can therefore be easily achieved.

The total yield over all stages (starting from diethylenetriamine) is 72.3%.

Compounds of general formula m are obtained from the compound of general formula IV

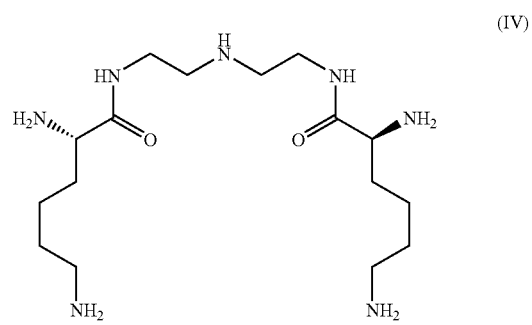

(IV)

whereby some or all amino groups can be present in salinized form with organic or inorganic acids, such as, e.g., p-toluenesulfonic acid, camphorsulfonic acid, methanesulfonic acid, benzenesulfonic acid, naphthalenesulfonic acid, acetic acid, benzoic acid, HCl or $H_2SO_4$, by reaction with compounds of general formula V

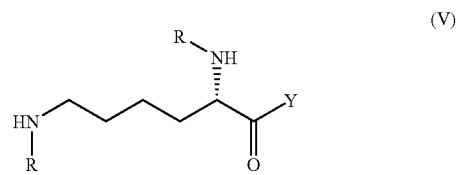

(V)

in which R stands for Z or Boc, and Y stands for the radicals

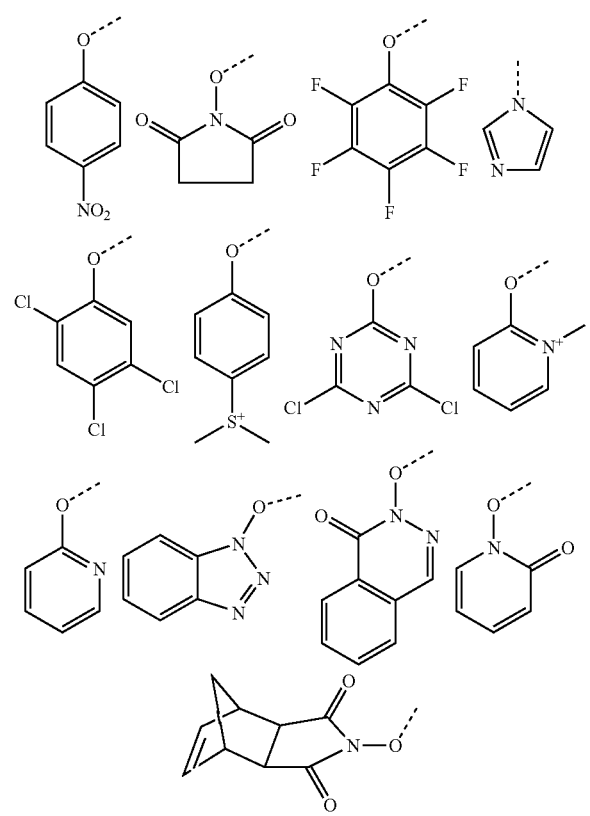

The reaction is carried out in solvents, such as, e.g., THF, 1-methyl-THF, dioxane, dichloromethane, chloroform, DMF, N-methylpyrrolidone, DMSO, methanol, ethanol, isopropanol, 1-butanol, 2-butanol or mixtures thereof; preferred are isopropanol and 2-butanol, as well as in a mixture with dichloromethane. Especially preferred is isopropanol in a mixture with dichloromethane at temperatures of 10 to 120° C., preferably 30–90° C.

As bases optionally to be used in the reaction, either organic bases, such as triethylamine, Hünig base, tributylamine, pyridine, or lutidine, or inorganic bases, such as sodium carbonate, potassium carbonate, or lithium carbonate, which are added to the reaction solution in solid form, can. Triethylamine is preferably used.

The reaction times are 1–15 hours, preferably 3–10 hours.

The crystallization of compounds III is carried out preferably from acetone (optionally with the addition of triethylamine).

Additional reactions are described in:

Tsvetkov, D. E.; Cheshev, P. E.; Tuzikov, A. B.; Chinarev, A. A.; Pazynina, G. V.; Sablina, M. A.; Gambaryan, A. S.; Bovin, N. V.; Rieben, R.; Shashkov, A. S.; Nifant'ev, N. E.; Russ. J. Bioorg. Chem. (Engl. Transl.); 28; 6; 2002; 470–486; Bioorg. Khim.; 28; 6; 2002; 518–534.

Kasuya, Yuji; Lu, Zheng-Rong; Kopeckova, Pavla; Tabibi, S. Esmail; Kopecek, Jindrich; Pharm. Res.; 19; 2; 2002; 115–123.

Gagnon, Paul; Huang, Xicai; Therrien, Eric; Keillor, Jeffrey W.; Tetrahedron Lett.; 43; 43; 2002; 7717–7720.

Bergeron, Raymond J.; Huang, Guangfei; Smith, Richard E.; Bharti, Neelam; McManis, James S.; Butler, Alison; Tetrahedron; 59; 11; 2003; 2007–2014. Gagnon, Paul; Huang, Xicai; Therrien, Eric; Keillor, Jeffrey W.; Tetrahedron Lett.; 43; 43; 2002; 7717–7720.

Mirgorodskaya, A. B.; Kudryavtseva, L. A.; Zuev, Yu. F.; Vylegzhanina, N. N.; Russ. J. Phys. Chem. (Engl. Transl.); 76; 11; 2002; 1849–1852; Zh. Fiz. Khim.; 76; 11; 2002; 2033–2036.

Xue, Jie; Guo, Zhongwu; J. Org. Chem.; 68; 7; 2003; 2713–2719.

Tanaka, Yasuko; Nakahara, Yuko; Hojo, Hironobu; Nakahara, Yoshiaki; Tetrahedron; 59; 23; 2003; 4059–4068.

Kovacs, J. et al.; J. Org. Chem.; 38; 1973; 2518–2521.

Kisfaludy, L. et al.; JLACBF; Justus Liebigs Ann. Chem.; 1973; 1421–1429.

Rostovtseva, L. I. et al.; J. Gen. Chem. USSR (Engl. Transl.); 41; 1971; 1385–1390; Zh. Obshch. Khim.; 41; 1971; 1380–1386.

Paquet, A.; Can. J. Chem.; 54; 1976; 733–737.

Miroshnikov, A. I. et al.; J. Gen. Chem. USSR (Engl. Transl.); 40; 2; 1970; 395–407; Zh. Obshch. Khim.; 40; 2; 1970; 429–443.

Wuensch, E. et al.; Hoppe-Seyler's Z. Physiol. Chem.; 357; 1976; 447–458.

The compound of formula IV is obtained from compounds of general formula VI

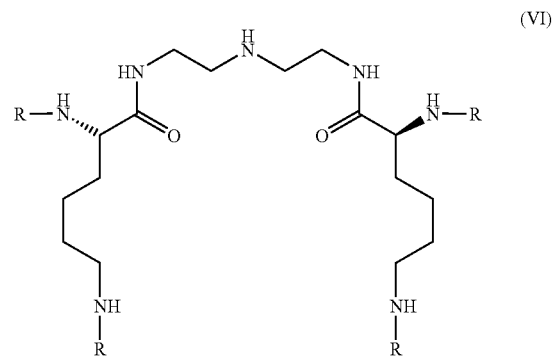

(VI)

in the case of R=Z by reaction with HBr or catalytic hydrogenation, whereby the catalytic hydrogenation is preferred. As a solvent, ethanol, methanol, isopropanol or THF is suitable. Especially preferred is ethanol. The hydrogenation is carried out at temperatures of between 10–70° C., but preferably at 20° C. The pressure is 5–20 bar; hydrogenation is preferably at 8–10 bar. The reaction times are determined by monitoring the hydrogen pressure (in a shutdown, TLC is provided and then a decision is made whether to continue hydrogenation or to discontinue it).

Methods of Z-group cleavage are known to one skilled in the art and are described in, e.g., Theodora W. Greene, Peter G. M. Wuts, "Protective Groups in Organic Chemistry" 3$^{rd}$ Ed., John Wiley & Sons, Inc. New York/Weinheim.

In the case of R=Boc, the reaction is performed with an acid, such as trifluoroacetic acid, HCl, HBr, H$_2$SO$_4$, or methanesulfonic acid.

Methods of Boc-group cleavage are known to one skilled in the art and are described in, e.g., Theodora W. Greene, Peter G. M. Wuts, "Protective Groups in Organic Chemistry" 3$^{rd}$ Ed., John Wiley & Sons, Inc. New York/Weinheim.

Compounds of general formula VI can be obtained from compounds of general formula V by reaction with diethylenetriamine.

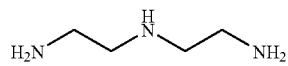

The reaction is carried out in solvents, such as, e.g., THF, 1-methyl-THF, tetrahydropyran, toluene, dioxane, dichloromethane, chloroform, or isopropanol (THF is preferred) at temperatures from 10 to 120° C., preferably 30–90° C.

As bases that are optionally to be used, either organic bases, such as triethylamine, Hünig base, tributylamine, pyridine, or lutidine, or inorganic bases, such as sodium carbonate, potassium carbonate, or lithium carbonate, which are added to the reaction solution in solid form, can be used.

The reaction times are 1–5 hours, preferably 1–2 hours.

The crystallization of the compounds that are obtained is carried out preferably from acetone (optionally with the addition of triethylamine).

Additional reactions are described in:

Tsvetkov, D. E.; Cheshev, P. E.; Tuzikov, A. B.; Chinarev, A. A.; Pazynina, G. V.; Sablina, M. A.; Gambaryan, A. S.; Bovin, N. V.; Rieben, R.; Shashkov, A. S.; Nifant'ev, N. E.;

Russ. J. Bioorg. Chem. (Engl. Transl.); 28; 6; 2002; 470–486; Bioorg. Khim.; 28; 6; 2002; 518–534.

Kasuya, Yuji; Lu, Zheng-Rong; Kopeckova, Pavla; Tabibi, S. Esmail; Kopecek, Jindrich; Pharm. Res.; 19; 2; 2002; 115–123.

Gagnon, Paul; Huang, Xicai; Therrien, Eric; Keillor, Jeffrey W.; Tetrahedron Lett.; 43; 43; 2002; 7717–7720.

Bergeron, Raymond J.; Huang, Guangfei; Smith, Richard E.; Bharti, Neelam; McManis, Janes S.; Butler, Alison; Tetrahedron; 59; 11; 2003; 2007–2014.

Gagnon, Paul; Huang, Xicai; Therrien, Eric; Keillor, Jeffrey W.; Tetrahedron Lett.; 43; 43; 2002; 7717–7720.

Mirgorodskaya, A. B.; Kudryavtseva, L. A.; Zuev, Yu. F.; Vylegzhanina, N. N.; Russ. J. Phys. Chem. (Engl. Transl.); 76; 11; 2002; 1849–1852; Zh. Fiz. Khim.; 76; 11; 2002; 2033–2036.

Xue, Jie; Guo, Zhongwu; J. Org. Chem.; 68; 7; 2003; 2713–2719.

Tanaka, Yasuko; Nakahara, Yuko; Hojo, Hironobu; Nakahara, Yoshiaki; Tetrahedron; 59; 23; 2003; 4059–4068.

Kovacs, J. et al.; J. Org. Chem.; 38; 1973; 2518–2521.

Kisfaludy, L. et al.; JLACBF; Justus Liebigs Ann. Chem.; 1973; 1421–1429.

Rostovtseva, L. I. et al.; J. Gen. Chem. USSR (Engl. Transl.); 41; 1971; 1385–1390; Zh. Obshch. Khim.; 41; 1971; 1380–1386.

Paquet, A.; Can. J. Chem.; 54; 1976; 733–737.

Miroshnikov, A. I. et al.; J. Gen. Chem. USSR (Engl. Transl.); 40; 2; 1970; 395–407; Zh. Obshch. Khim.; 40; 2; 1970; 429–443.

Wuensch, E. et al.; Hoppe-Seyler's Z. Physiol. Chem.; 357; 1976; 447–458.

Compounds of general formula V can be produced from commercially available Di-Boc or Di-Z-(L)-lysine according to methods of acid activation that are known to one skilled in the art. The processes that are described here can also be performed with the more expensive (D)-lysine.

Activations to the corresponding active esters are described in the bibliographic references below:

4-Nitrophenol-ester:
Wuensch, E. et al.; Chem. Ber.; 97; 1964; 1819–1828
Sandrin, E.; Boissonnas, R. A.; Helv. Chim. Acta; 46; 1963; 1637–1669.
Hofmann, K. et al.; J. Amer. Chem. Soc.; 87; 1965; 611–619.

N-Succinimide-ester:
Miroshnikova, 0. V.; Berdnikova, T. F.; Olsufyeva, E. N.; Pavlov, A. Y.; Reznikova, M. I.; et al.; J. Antibiot.; 49; 11; 1996; 1157–1161.
Malabarba, Adriano; Ciabatti, Romeo; Gerli, Erminio; Ripamonti, Franca; Ferrari, Pietro; et al.; J. Antibiot.; 50; 1; 1997; 70–81.
Marquisee; Kauer; J. Med. Chem.; 21; 1978; 1188, 1191.
Garcia-Lopez, M. Teresa; Gonzalez-Muniz, Rosario; Molinero, M. Teresa; Naranjo, Jose R.; R10, J. Del; J. Med. Chem.; 30; 9; 1987; 1658–1663.

Pentafluorophenol-ester:
Schoen, Istvan; Szirtes, Tamas; Ueberhardt, Tamas; Csehi, Attila; J. Org. Chem.; 48; 11; 1983; 1916–1919.
Il'ina, A. V.; Davidovich, Yu. A.; Rogozhin, S. V.; Bull. Acad. Sci. USSR Div. Chem. Sci. (Engl. Transl.); 37; 12; 1988; 2539–2541; Izv. Akad. Nauk SSSR Ser. Khim.; 12; 1988; 2816–2818.
Kisfaludy, L. et al.; J. Org. Chem.; 35; 10; 1970; 3563–3565.

Imidazoyl-amide:
Miyazaki, Koichi; Kobayashi, Motohiro; Natsume, Tsugitaka; Gondo, Masaaki; Mikami, Takashi; et al.; Chem. Pharm. Bull.; 43; 10; 1995; 1706–1718.

Use of the Z group is generally preferred.

The examples below are used for an explanation of the subject of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

Production of Z-24-Amine

1a)

N,N'-(Iminodiethane-2,1-diyl)-bis{N2,N6-bis[(benzyloxy)carbonyl]-L-lysinamide}

992 g (9.615 mol) of diethylenetriamine is introduced at 20° C. and mixed with 30 l of THF. The clear colorless solution is refluxed. While being heated, a solution that consists of 10 kg (18.672 mol) of Lysonip, dissolved in 30 l of THF, is added in drops within one hour to this solution. It is stirred for one hour at reflux. 35 l of solvent is distilled off under normal pressure at a shell temperature of 90° C. Then, it is redistilled on acetone by repeated addition of acetone (until the refraction index of the distillate has reached a value of <1.361/volume of the reaction solution about 40 l). 80 l of acetone and 1.896 kg of triethylamine (28.1 mol) are added and refluxed for one hour. It is cooled to 10° C., and precipitated crystal paste is filtered off. It is rewashed with 100 l of acetone. The product that is still acetone-moistened is re-added in 100 l of acetone and refluxed for one-hour. After cooling to 10° C., it is filtered and rewashed with 10 l of acetone. Then, the product is dried at 40° C. (16 hours) under nitrogen ambient air.

Yield: 8.2 kg of colorless solid (95% of theory)

| Elementary analysis: | | | |
|---|---|---|---|
| Cld. | C 64.34 | H 6.86 | 10.94 |
| Fnd. | C 64.17 | H 7.02 | 10.83 |

1 b)

N,N'-(Iminodiethane-2,1-diyl)-bis(L-lysinediamide), Pentatosylate 20.00 kg (22.32 mol) of the title compound of Example 1a is introduced into 100 l of ethanol, and 23.5 kg (122.76 mol) of p-toluenesulfonic acid-monohydrate (water content 9–13%) and 0.8 kg of palladium catalyst (Pd/C 10% E 101 N/W) are added. While being stirred, it is hydrogenated at 8 bar until hydrogen absorption is halted.

Catalyst is filtered out, and it is rewashed twice with about 20 l of ethanol. The solution is used without further working-up in the next step. In this case, it is redistilled on isopropanol.

Yield: 27.2 kg (100% of theory)

For analytical characterization, a sample was evaporated to the dry state and provided for elementary analysis:

| Elementary analysis: | | | | |
|---|---|---|---|---|
| Cld. | C 50.19 | H 6.36 | N 8.03 | S 13.13 |
| Fnd. | C 50.04 | 6.49 | N 7.89 | S 13.02 |

1 c)

N,N'-(Iminodiethane-2,1-diyl)-bis(N-2-{N2,N6-bis[(benzyloxy)carbonyl]-L-lysyl}-N-6-{N2,N6-bis[(benzyloxy)carbonyl]-L-lysyl}-L-lysinamide)

52.1 kg (42.71 mol) of the title compound of Example 1b), dissolved in 520 l of isopropanol (redistilled isopropanolic solution), is introduced at room temperature and heated to the shell temperature of 80° C. It is allowed to stir for 15 more minutes at this temperature, and 23.8 kg (234.9 mol) of triethylamine is added. A solution that consists of 100.7 kg (187.9 mol) of Lysonip, dissolved in 200 l of dichloromethane, is added in drops to the above within 2 hours and stirred for 6 more hours at a shell temperature of 80° C. (internal temperature about 65–70° C.). The solvent is distilled off as much as possible (up to a still stirrable paste). Then, it is redistilled to acetone by repeated addition of acetone. The readily stirrable yellow suspension is mixed with 1050 l of acetone and then with 38.0 kg (376.0 mol) of triethylamine. The suspension is stirred under reflux for 1 hour and then cooled to room temperature and stirred for one more hour. The product is filtered off and rewashed with 250 l of acetone. The moist crystallizate is introduced into 1050 l of acetone and then mixed with 19.0 kg (188.0 mol) of triethylamine. The suspension is stirred under reflux for one hour (shell temperature 80° C.), and then cooled to room temperature. The solid is filtered off and rewashed with 250 l of acetone. The product is dried for about 20 hours at 50° C. in a vacuum-drying oven (100 mbar).

Yield: 78.1 kg of colorless solid (94% of theory)

| Elementary Analysis: | | | |
|---|---|---|---|
| Cld. | C 64.21 | H 6.89 | N 10.80 |
| Fnd. | C 64.12 | H 6.98 | N 10.67 |

1 d)

N,N',N'',N''',N'''',N'''''-[Benzene-1,3,5-triyl-tris(carbonylnitrilodi-2,1-ethanediyl)]-hexakis{N2-[N2,N6-bis(benzyloxycarbonyl)-L-lysyl]-N-6-[N2,N6-bis(benzyloxy carbonyl)-L-lysyl]-L-lysinamide}

10.11 kg (5.196 mol) of the title compound of Example 1c) is introduced with 200 l of THF (water content: <0.007%), and 526 g (5.198 mol) of triethylamine (water content: <0.048%) is added and heated to a shell temperature of 85° C. In the meantime, a solution that consists of 400.00 g (1.507 mol) of trimesic acid trichloride, dissolved in 10 l of THF, is produced under nitrogen. This solution is added in drops within 30 minutes at a shell temperature of 85° C. (IT ~65° C.). After the addition is completed, it is stirred for 60 more minutes at a shell temperature of 85° C. A slightly cloudy solution is present. It is stirred for 30 more minutes. It is allowed to cool to an IT of 40° C., and 4.67 g of activated carbon Carbopal P 3 is added, and it is stirred for 1 more hour. In this case, it is allowed to cool to an IT of 25° C. The activated carbon is filtered off on 5 kg of silica gel (Matrex 35–70μ), it is rewashed twice with 20 l each of THF, and the filtrate is concentrated by evaporation in a vacuum as much as possible (to a still stirrable solution).

Then, a chromatographic purification is performed. To this end, the application solution is first produced:

In the solution that is largely concentrated by evaporation, it is redistilled to methanol by repeated addition of methanol (up to about 30 l of volume), and then 2 l of THF is added. The thus obtained solution is used for chromatography.

It is chromatographed on YMC-ODS/10 um of 100 A/mobile solvent=methanol/water 4:1 (several passes).

The product-containing solutions are combined and largely concentrated by evaporation in a vacuum. The product can be isolated either by spray-drying as a solid or else redistilled on the solvent for the next step.

Yield: 25.2 kg (81% of theory)

For the analytical characterization, a sample was evaporated to the dry state and provided for elementary analysis:

| Elementary Analysis: | | | |
|---|---|---|---|
| Fnd. | C 64.35 | H 6.71 | N 10.52 |
| Cld. | C 64.19 | H 6.86 | N 10.41 |

Total yield of the process for the production of Z-24-amine:

Total yield (over 4 stages, starting from diethylenetriamine): 72.3% of theory.

The entire disclosures of all applications, patents and publications, cited herein and of corresponding German application No. 10361140.1, filed Dec. 16, 2003 and U.S. Provisional Application Ser. No. 60/536,503, filed Jan. 15, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of compounds of formula I

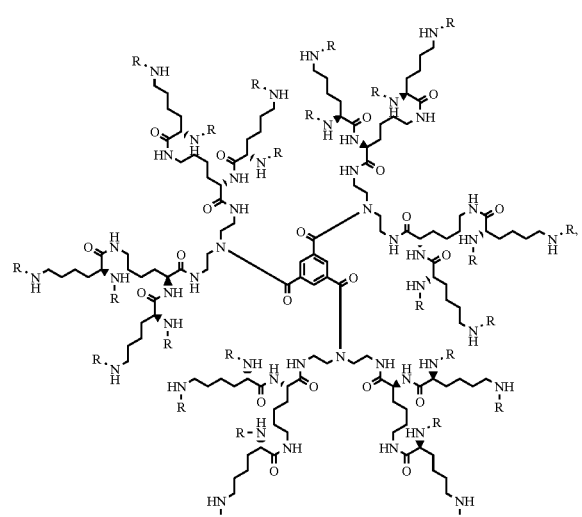

in which R stands for a Z or a Boc protective group, which comprises reacting a compound of formula II:

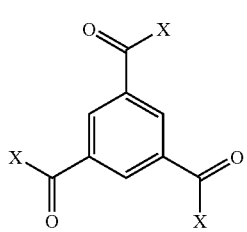

in which X stands for a Cl, Br, or F atom or a 4-nitrophenol, N-succinimide, imidazole, or pentafluorophenol group, with a compound of formula III:

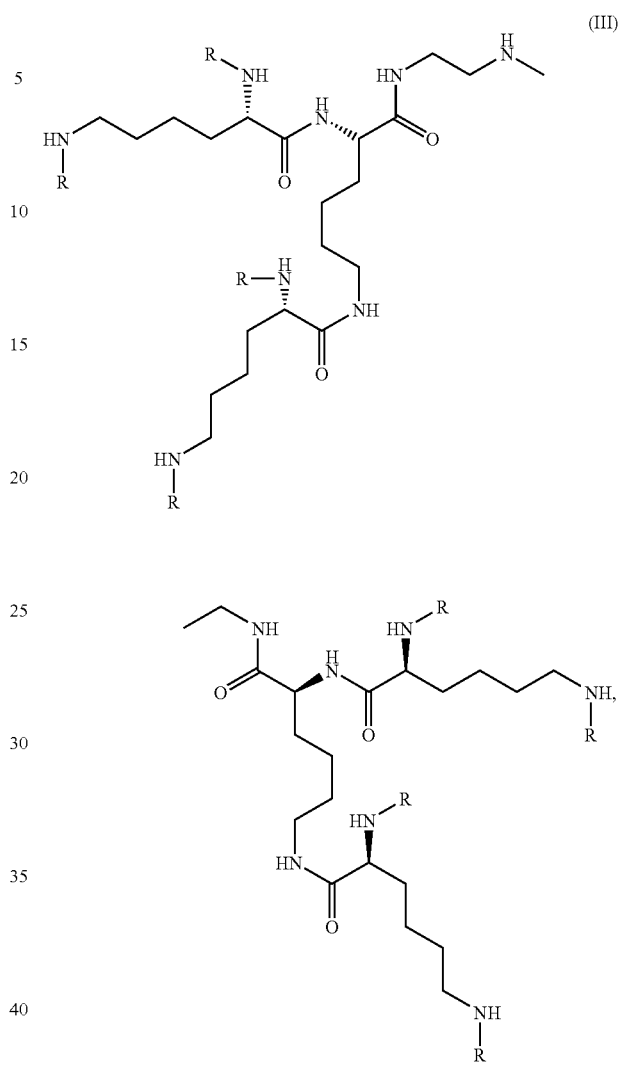

in which R stands for a Z or Boc group, in a non-protic solvent with use of an acid trap at a temperature of 0–100° C. within 30 minutes to 5 hours.

2. A process according to claim 1, wherein THF, 1-methyl-THF, tetrahydropyran, dichloromethane, 1,2-dimethoxyethane, dioxane, acetonitrile, propionitrile or chloroform is used as the non-protic solvent.

3. A process according to claim 1, wherein an organic base is used as the acid trap.

4. A process according to claim 1, wherein an inorganic base is used as the acid trap.

5. A process according to claim 3, wherein triethylamine, Hünig base, tributylamine, pyridine or lutidine is used as the acid trap.

6. A process according to claim 4, wherein sodium carbonate, potassium carbonate or lithium carbonate is used as the acid trap.

7. A process according to claim 1, wherein the operation is performed at a temperature of 50–80° C.

8. A process according to claim 1, wherein the reaction is performed within 0.5 to 2.5 hours.

9. A compound of formula III:

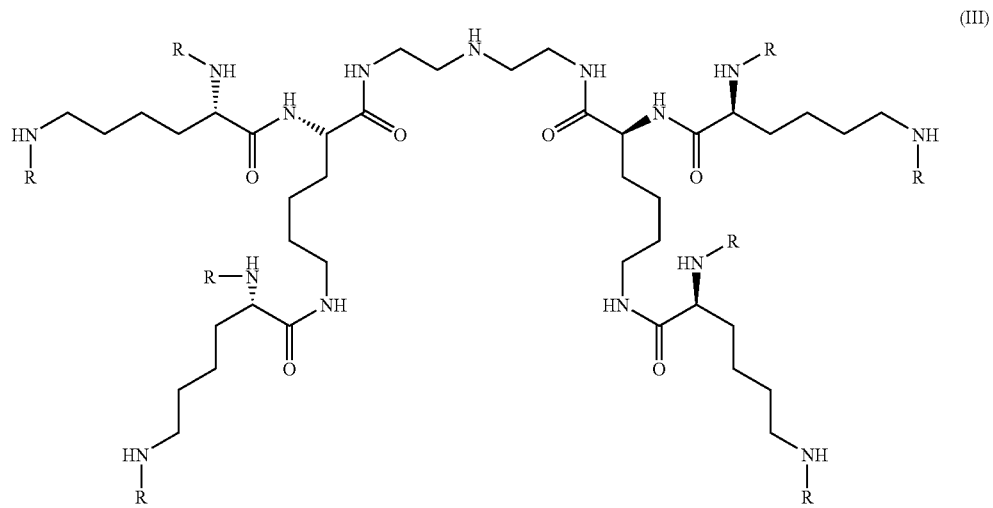

wherein R is a Z or Boc protective group.

10. The process of claim 1, further comprising cleaving the Z or Boc protective groups and converting the resulting amine to the Gadomer target compound by reaction with active esters of complexing agents.

11. The process of claim 1, wherein X in the formula II compounds is a Cl atom.

12. The process of claim 1, wherein the non-protic solvent is THF.

13. The process of claim 1, wherein the reaction is carried out at a temperature of from 50–80° C.

14. The process of claim 1, wherein the reaction is carried out for 30 minutes to 2.5 hours.

15. The process of claim 1, wherein R is a Z protective group.

16. The process of claim 1, wherein R is a Boc protective group.

17. The process of claim 1, further comprising purifying the crude product from the reaction by chromatography on normal or reversed-phase phases.

18. The process of claim 17, wherein the chromatography is a reversed-phase chromatography with a water-miscible mobile solvent.

19. The process of claim 18, wherein water-miscible solvent is selected from the group consisting of methanol, ethanol, acetonitrile, isopropanol, acetone and their mixtures with water.

20. The process of claim 18, further comprising isolating the product by spray-drying or by redistillation.

* * * * *